United States Patent
Virk et al.

(10) Patent No.: US 10,517,905 B1
(45) Date of Patent: Dec. 31, 2019

(54) FABRICATION OF PROBIOTICS NANOWHISKERS USING CHEESE

(71) Applicant: KING SAUD UNIVERSITY, Riyadh (SA)

(72) Inventors: Promy Virk, Riyadh (SA); Manal Ahmed Gasmelseed Awad, Riyadh (SA); Mai Abdelrahman Elobeid, Riyadh (SA); Khalid Mustafa Osman Ortashi, Riyadh (SA); Awatif Ahmed Hendi, Riyadh (SA)

(73) Assignee: King Saud University, Riyadh (SA)

( * ) Notice: Subject to any disclaimer, the term of this patent is extended or adjusted under 35 U.S.C. 154(b) by 12 days.

(21) Appl. No.: 16/127,470

(22) Filed: Sep. 11, 2018

(51) Int. Cl.
| | |
|---|---|
| A61K 35/741 | (2015.01) |
| A61P 3/00 | (2006.01) |
| A61P 39/00 | (2006.01) |
| A23C 19/086 | (2006.01) |
| A23C 19/09 | (2006.01) |
| A23L 33/135 | (2016.01) |

(52) U.S. Cl.
CPC .......... *A61K 35/741* (2013.01); *A23C 19/086* (2013.01); *A23C 19/09* (2013.01); *A23L 33/135* (2016.08); *A61P 3/00* (2018.01); *A61P 39/00* (2018.01); *A23V 2002/00* (2013.01)

(58) Field of Classification Search
CPC .... A61K 35/741; A23L 33/135; A23C 19/086
See application file for complete search history.

(56) References Cited

U.S. PATENT DOCUMENTS 9,623,067 B1 *  4/2017 Awad .................. A61K 36/889
2008/0254165 A1  10/2008 Patel et al.

FOREIGN PATENT DOCUMENTS

GB  192028925  5/1910
RU  2013126936 A  12/2014

OTHER PUBLICATIONS

Nancib et al. Use of date products in production of the thermophilic dairy starter strain *Streptococcus thermophiles* BioresourceTechnology67 (1999) 291-295.*
Angellier et al., "Waxy Maize Starch Nonocrystals as Filler in Natural Rubber", Macromolecular Symposia, vol. 233, Issue 1, Feb. 2006, pp. 132-136.
Castro, J.M. et al., "Biocheese: A Food Probiotic Carrier", BioMed Research International, Review Article, Oct. 21, 2014, pp. 1-11.
Sekhon, Bhupinder S., "Food nanotechnology—an overview", Nanotechnology, Science and Applications, Review, Dovepress, 2010:3, pp. 1-15.
Jama, Adel M. et al., "Protective Effect of Probiotic Bacteria Against Cadmium-Induced Genotoxicity in Rat Hepartocytes in Vivo and in Vitro", Arch. Biol. Sci., Belgrade, 64 (3), 2013, pp. 1197-1206.
Angellier et al., "Optimization of the Preparation of Aqueous Suspensions of Waxy Maize Starch Nanocrystals Using a Response Surface Methodology", Biomacromolecules, 2004, vol. 5, No. 4, pp. 1545-1551.

* cited by examiner

*Primary Examiner* — Louise W Humphrey
*Assistant Examiner* — Stephen A Perkins
(74) *Attorney, Agent, or Firm* — Richard C. Litman; Nath, Goldberg & Meyer

(57) ABSTRACT

A method of fabricating probiotics nanowhiskers using cheese comprises cutting and grinding cheese to produce cheese powder; mixing the cheese powder with sulfuric acid to produce a solution; stirring the solution to produce a stirred solution; and filtering the stirred solution to produce the probiotics nanowhiskers. The fabricated probiotics nanowhiskers possess antioxidant, anti-inflammatory, antitumor, and antimicrobial properties. The probiotics nanowhiskers may reduce cadmium concentration in a patient's liver. The probiotics nanowhiskers may also ameliorate the oxidative stress assessed as a decrease in the serum MDA levels in a patient.

2 Claims, 4 Drawing Sheets

FABRICATION OF PROBIOTICS NANOWHISKERS USING CHEESE

BACKGROUND

1. Field

The disclosure of the present patent application generally relates to probiotics, and particularly relates to fabrication of probiotics nanowhiskers using cheese powder and the related evaluation of antioxidant potential against cadmium-induced toxicity.

2. Description of the Related Art

If foods contain some health-promoting components beyond traditional nutrients, the foods may be categorized as functional foods. For instance, foods can be modified to become functional by adding probiotics.

Probiotic foods are typically processed products containing viable probiotic microorganisms. The food delivery system contains the microorganisms in a suitable matrix and sufficient concentration. Generally, probiotic cultures have found success in freshly fermented dairy food delivery systems, such as yogurts and fermented milks.

Probiotics are live bacteria and yeasts generally recognized to be beneficial to the digestive system. For instance, probiotics may help prevent symptoms of irritable bowel syndrome and diarrhea caused by infections or antibiotics. Common bacteria microorganisms in probiotics include those in the bacteria groups *Lactobacillus* and *Bifidobacterium*, and *Saccharomyces boulardii* is yeast found in probiotics.

Several studies have been conducted related to the health benefits of ingesting probiotic-containing foods. While some benefits have been proven scientifically, other benefits require further research and studies in humans. However, the science-based benefits generally related to probiotics include antimicrobial and antimutagenic activities; anticarcinogenic properties; antihypertension properties; beneficial effects on mineral metabolism, especially regarding bone stability; attenuation of symptoms of bowel disease and Crohn's syndrome; reduction of symptoms of food allergies; and reduction of LDL-cholesterol levels.

With the health benefits seen so far through probiotics, there is a need to expand the available probiotics-containing options. Thus, a fabrication of probiotics nanowhiskers using cheese solves the aforementioned problem.

SUMMARY

In an embodiment, the present subject matter is directed to a method of fabricating probiotics nanowhiskers using cheese, which includes grinding cheese to produce cheese powder; mixing the cheese powder with sulfuric acid to produce a solution; and filtering the stirred solution to provide the probiotics nanowhiskers.

For example, in a non-limiting embodiment, the present subject matter is directed to a method of fabricating probiotics nanowhiskers using cheese, comprising: cutting cheese into small pieces and drying; grinding the dried cheese in a heavy-duty grinder; passing the resulting ground particles through 1-2 mm screens, producing cheese powder; weighing cheese powder and adding 3.16M sulfuric acid solution to the weighed cheese powder to create a cheese powder solution; stirring the cheese powder solution at a speed of 100 rpm; and filtering the stirred cheese powder solution through a Millipore filter having a pore size of 220 nm to produce probiotics nanowhiskers.

In an embodiment, the present subject matter is directed to the probiotics nanowhiskers fabricated according to such a method.

Further, the probiotics nanowhiskers fabricated according to the present subject matter may be used to reduce cadmium levels and oxidative stress based on the serum MDA levels in a patient. In one embodiment, the present subject matter is directed to a method of reducing cadmium levels in a patient comprising: administering the probiotics nanowhiskers to a patient in need thereof; wherein treatment of the patient with the probiotics nanowhiskers for a specified amount of time reduces cadmium levels in a liver of the patient. In another embodiment, the present subject matter is directed to a method of reducing serum MDA levels in a patient comprising: administering the probiotics nanowhiskers to a patient in need thereof; wherein treatment of the patient with the probiotics nanowhiskers for a specified amount of time reduces serum MDA levels in the patient.

These and other features of the present disclosure will become readily apparent upon further review of the following specification and drawings.

DETAILED DESCRIPTION OF THE PREFERRED EMBODIMENTS

Figure 1:
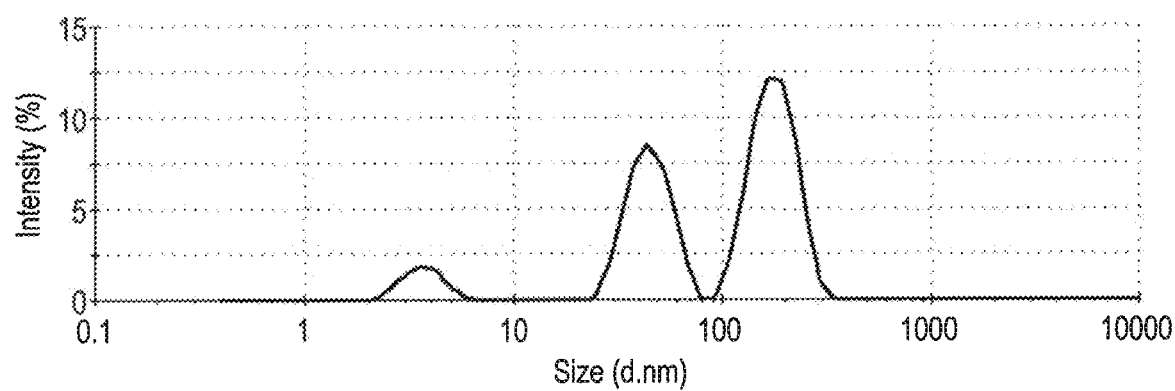
FIG. 1 shows a graph of Zeta sizer for measuring the average particle size of the nanowhiskers.
Figure 2:
FIG. 2 shows a transmission electron microscopy (TEM) image of nanowhiskers prepared according to Example 1. Acc. Volt.: 100 kV. Mag.: 100000×.
Figure 3:
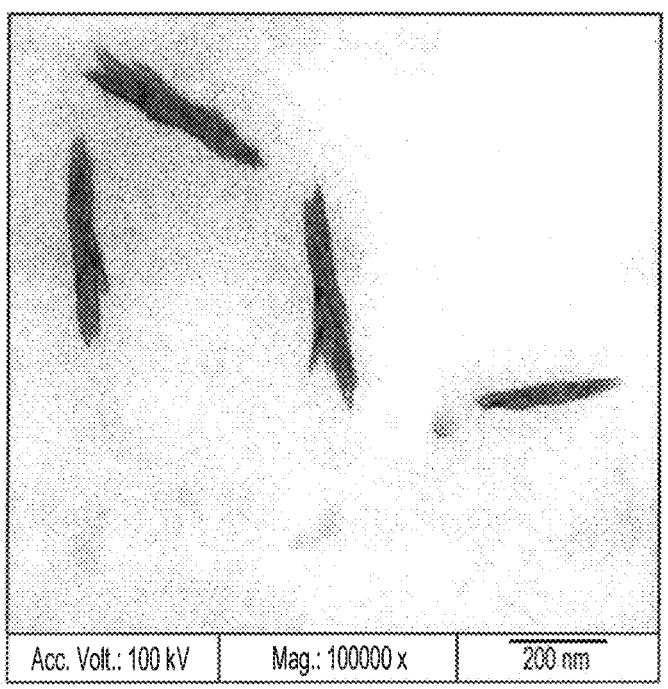
FIG. 3 shows a TEM image of nanowhiskers prepared according to Example 1. Acc. Volt.: 100 kV. Mag.: 100000×.
Figure 4:
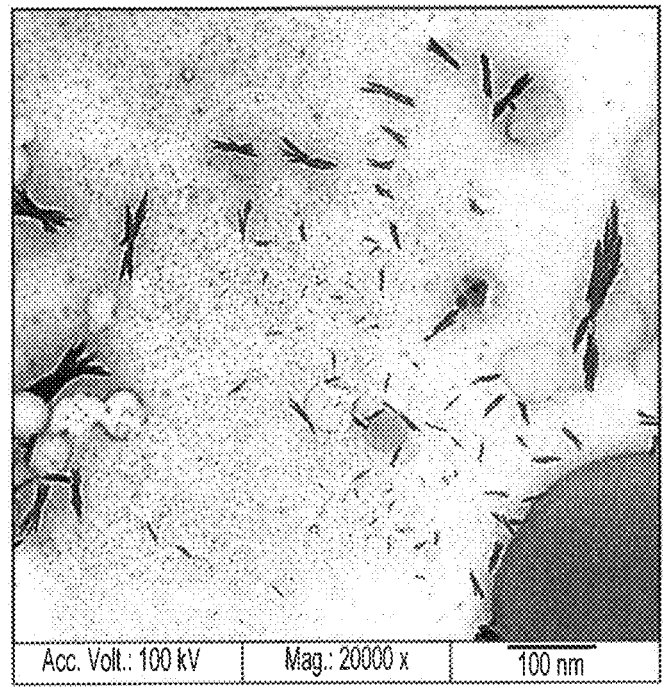
FIG. 4 shows a TEM image of nanowhiskers prepared according to Example 1. Acc. Volt.: 100 kV. Mag.: 20000×.
Figure 5:
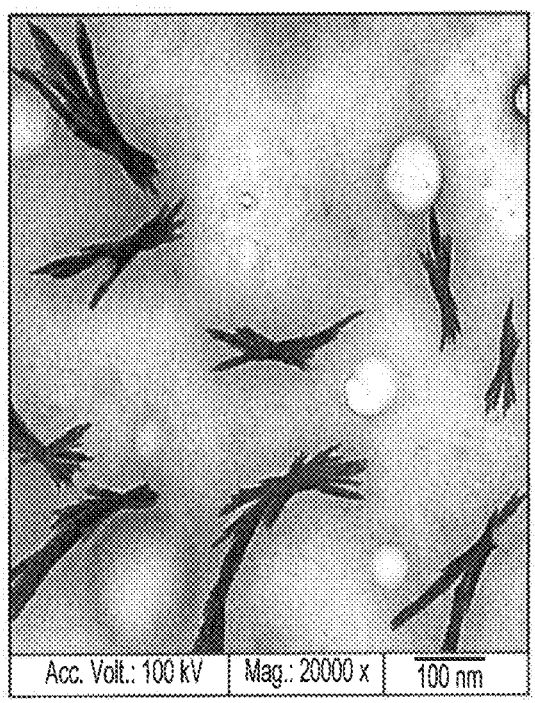
FIG. 5 shows a TEM image of nanowhiskers prepared according to Example 1. Acc. Volt.: 100 kV. Mag.: 20000×.
Figure 6:
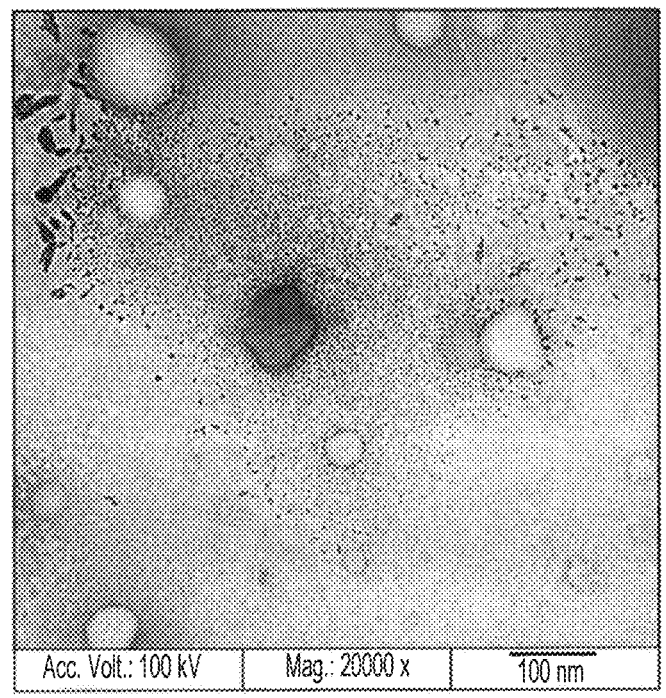
FIG. 6 shows a TEM image of nanowhiskers prepared according to Example 1. Acc. Volt.: 100 kV. Mag.: 20000×.
Figure 7:
FIG. 7 shows a TEM image of nanowhiskers prepared according to Example 1. Acc. Volt.: 100 kV. Mag.: 30000×.

In an exemplary embodiment, the present subject matter is directed to fabrication of probiotics nanowhiskers using cheese. The resulting nanowhiskers possess antioxidant, anti-inflammatory, antitumor, and antimicrobial properties.

In a non-limiting exemplary example, the probiotic nanowhiskers may stimulate the growth of microorganisms. The microorganisms may be selected from the *Lactobacillus* or *Bifidobacterium* species. As a further non-limiting example, the microorganisms may be selected from *L. acidophilus*, *L. casei*, *L. casei* ssp. *pseudoplantarum*, *L. casei* ssp. *rhamnosus*, *L. delbrueckii* ssp. *bulgaricus*, *L. delbrueckii* ssp. *lactis*, *L. gasseri*, *L. paracasei*, *L. plantarum*, *L. rhamnosus*, *L. salivarius*, *B. animalis*, *B. animalis* ssp. *lactis*, *B. breve*, *B. infantis*, *B. lactis*, *B. longum*, *Enterococcus faecalis*, *E. faecium*, *Lactococcus lactis*, *Leuconostoc paramesenteroides*, *Propionibacterium freudenreichii* ssp. *shermanii*, and *Streptococcus thermophilus*.

As a non-limiting example, the present subject matter is directed to a method comprising the steps of reducing cheese to a cheese powder. For example, the method can include cutting cheese into small pieces; grinding the cheese; and passing the ground cheese through screens having pore sizes of about 1 mm to about 2 mm to produce cheese flour (or cheese powder). The cheese powder can then be mixed with an acid, e.g., sulfuric acid ($H_2SO_4$) to provide a solution and the solution can be stirred for a period of time. The stirred solution can be filtered through a Millipore filter with a pore size of about 220 nm to provide the nanowhiskers. In an embodiment, the nanowhiskers can have a size ranging from about 3 nm to about 180 nm.

The present teachings are illustrated by the following examples.

Example 1: Formation of Probiotic Nanowhiskers

First, 10 g of cheese was cut into small pieces and dried. Then, the dried cheese was ground in a heavy-duty grinder until small enough to pass through 1-2 mm screens, producing cheese flour (or cheese powder), which was then kept until used.

Next, 3 g of cheese flour was weighed and 25 mL of 3.16M sulfuric acid solution was added to it. The flasks were kept under a stirrer at a speed of 100 rpm. The nanoparticles were filtered through a Millipore filter having a pore size of 220 nm. Cheese powder was subjected to acid hydrolysis according to the procedure of Angellier et al., 2006 (Waxy Maize Starch Nanocrystals as Filler in Natural Rubber) and Angellier et al., 2004 (Optimization of the Preparation of Aqueous Suspensions of Waxy Maize Starch Nanocrystals Using a Response Surface Methodology) to produce probiotics nanowhiskers.

Operative conditions leading to the smallest size of insoluble hydrolyzed residue within the shortest time and with the highest yield are described in Angellier et al., 2004. Compared to the traditional procedure of 40 days of HCl (hydrochloric acid) treatment with a yield of 0.5 wt %, Angellier et al., 2004 resulted in starch nanocrystals with a yield of 15 wt % after only 5 days of sulfuric acid ($H_2SO_4$) hydrolysis. In Angellier et al., 2006, acid hydrolysis is described wherein waxy maize starch nanocrystals were prepared by sulfuric acid hydrolysis of native waxy maize starch granules. The nanocrystals were observed in aggregate form with an average size of around 4.4 m in Angellier et al., 2006. In Angellier et al., 2004, the acid type, acid concentration, temperature, and hydrolysis duration were conditions studied.

In an embodiment of the present subject matter, sulfuric acid hydrolysis is used. The sulfuric acid hydrolysis can include: mixing the cheese powder with $H_2SO_4$ solution at a prescribed concentration, stirring continuously at a prescribed rate while maintaining a prescribed temperature for a prescribed time period, and then washing in distilled water to produce the probiotics nanowhiskers. As a non-limiting example, and in accordance with Angellier et al., 2004 and 2006, in the sulfuric acid hydrolysis of the present subject matter, the prescribed concentration of the $H_2SO_4$ solution is about 3.16M, the prescribed temperature is about 40° C., the prescribed rate is about 100 rpm, and the prescribed time period is about 5 days.

The nanoparticles were analyzed with the Zeta sizer (ZEN 3600, MALVERN, United Kingdom) for measurement of the average particle size. The Zeta sizer results are shown in FIG. 1. The Z-average (d·nm) is 415.4 d·nm, with Pdl of 0.461. Peak 1 shows a size (d·nm) 178.7, 55.9% intensity, with a standard deviation of 42.58 d·nm. Peak 2 shows a size (d·nm) 45.31, 37.0% intensity, with a standard deviation of 10.46 d·nm. Peak 3 shows a size (d·nm) 3.698 d·nm, 7.0% intensity, with a standard deviation of 0.7508 d·nm.

Images of the prepared nanoparticles were taken by transmission electron microscopy (TEM, JEM-1400, JEOL, Japan). FIGS. 2-7 show TEM images of the probiotics nanowhiskers fabricated from cheese.

Example 2: Determination of Cd Bioaccumulation in Tissues and Serum MDA Levels as a Biomarker of Oxidative Stress There are several practical and commercial applications of the present subject matter. For instance, as a non-limiting example, probiotics nanowhiskers fabricated from cheese possess potent antioxidant, anti-inflammatory, and antitumor properties, and can also be used for antimicrobial properties. To further explore the properties of the probiotics nanowhiskers, the following study was conducted.

Wistar rats were exposed to cadmium, which is a toxic non-essential element that is extremely harmful to humans and animals. For instance, cadmium is carcinogenic and induces reactive oxygen species and inhibits DNA repair. Studies have indicated that probiotic bacteria may play an important role in detoxification and elimination of cadmium in the human body. As such, one treatment option for the Wistar rats exposed to cadmium was the probiotics nanowhiskers fabricated from cheese.

Experimental Design

Adult male Wistar rats (n=20), weighing 150±10 g, were procured from the Animal House Facility at King Saud University, Riyadh. The rats were acclimated to the laboratory conditions at 22±2° C. in metabolic cages (6 rats/cage) and maintained under a 12 hour light/dark cycle. The rats were fed a commercial diet and given tap water ad libitum. After the period of acclimatization (7 days), rats were randomly allocated into three groups of 6 rats each. Each group was in duplicate.

The rats were gavaged with the following required doses. Group I, the control group, was administered physiological saline. Group II received $CdCl_2$ at a dose of 70 ppm in saline (Jama et al., 2012). Group III received both $CdCl_2$ (70 ppm) and cheese nanoparticles (1 ml containing 5×109 colony forming units (cfu)).

After an exposure period of five weeks, the blood samples were collected from all rats for the preparation of serum and plasma to assess the biochemical variables. The cadmium concentration was determined thereafter. A set of liver samples was kept for biochemical assays. All samples of serum, plasma, and tissue were stored at −80° C. until further analysis.

Results

An exposure of three weeks to $CdCl_2$, significantly (p≤0.05) increased the Cd concentration in the kidneys and liver of the rats as compared to the control group. However, in the muscles, no significant increase was observed upon Cd exposure. The treatment with the cheese nanoparticles significantly (p≤0.05) reduced the Cd levels in the liver as compared to the group exposed to Cd only. In the kidneys, the Cd levels were not affected by the treatment with the nanoparticles. The serum MDA levels were also significantly (p≤0.05) enhanced in the rats exposed to Cd as compared to the control group. Treatment with the cheese nanoparticles (ChNano) significantly (p≤0.05) reduced the MDA levels.

Thus, as shown in Table 1, the treatment with the cheese nanoparticles was effective in reducing the Cd levels in the liver and also alleviating the oxidative stress, as was evident by the reduced serum MDA levels.

TABLE 1

Lead Concentrations (μg/g) in Tissues and Serum MDA Levels of Rats

| Experimental Groups | Cd Concentration in the Tissues (μg/g) | | | Serum, MDA Levels (nmol/ml) |
|---|---|---|---|---|
| | Liver | Kidneys | Muscles | |
| Control | 27.90 ± 7.23$^a$ | 42.36 ± 8.86$^a$ | 41.06 ± 6.62$^a$ | 0.80 ± 0.02$^a$ |
| Cd | 317.26 ± 19.60$^b$ | 293.84 ± 35.34$^b$ | 55.50 ± 14.01$^a$ | 1.50 ± 0.19$^b$ |
| Cd + CbNano | 266.40 ± 31.34$^c$ | 271.31 ± 55.48$^b$ | 42.46 ± 7.76$^a$ | 0.95 ± 0.06$^a$ |

Values with the different superscript letter within each column are significantly different at 5% level of probability (p ≤ 0.05).
Values are mean ± SEM, n = 5.

It is to be understood that the fabrication of probiotics nanowhiskers using cheese is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of producing cheese nanoparticles, comprising:
    cutting a cheese into pieces;
    drying the cheese pieces;
    grinding the dried cheese pieces to provide cheese particles;
    passing the cheese particles through screens having pore sizes of 1 mm to 2 mm to provide cheese powder;
    adding the cheese powder to a 3.16M sulfuric acid solution to create a cheese powder solution;
    stirring the cheese powder solution at a speed of 100 rpm at a temperature of 40° C.; and
    filtering the stirred cheese powder solution through a filter having a pore size of 220 nm to produce the cheese nanoparticles.

2. Cheese nanoparticles, wherein the cheese nanoparticles are produced according to the method of claim 1.

* * * * *